United States Patent

Kasic, II

(10) Patent No.: US 8,287,562 B2
(45) Date of Patent: Oct. 16, 2012

(54) SWALLOWABLE SELF-EXPANDING GASTRIC SPACE OCCUPYING DEVICE

(75) Inventor: James Kasic, II, Boulder, CO (US)

(73) Assignee: 7L, LLC, Boulder, CO (US)

( * ) Notice: Subject to any disclaimer, the term of this patent is extended or adjusted under 35 U.S.C. 154(b) by 607 days.

(21) Appl. No.: 12/340,024

(22) Filed: Dec. 19, 2008

(65) Prior Publication Data

US 2009/0192535 A1     Jul. 30, 2009

Related U.S. Application Data

(60) Provisional application No. 61/015,269, filed on Dec. 20, 2007.

(51) Int. Cl.
*A61M 29/00* (2006.01)
*A61F 2/00* (2006.01)

(52) U.S. Cl. .......................... 606/192; 600/37

(58) Field of Classification Search .................. 606/192, 606/195–197; 623/23.68; 600/37
See application file for complete search history.

(56) References Cited

U.S. PATENT DOCUMENTS

| | | |
|---|---|---|
| 3,551,556 A | 12/1970 | Kliment et al. |
| 3,944,064 A | 3/1976 | Bashaw et al. |
| 4,178,361 A | 12/1979 | Cohen et al. |
| 4,739,758 A | 4/1988 | Lai et al. |
| 4,812,315 A | 3/1989 | Tarabishi |
| 5,049,106 A | 9/1991 | Kim et al. |
| 5,129,915 A | 7/1992 | Cantenys |
| 5,336,486 A | 8/1994 | Acharya |
| 5,750,585 A | 5/1998 | Park et al. |
| 6,160,084 A | 12/2000 | Langer et al. |
| 6,271,278 B1 | 8/2001 | Park et al. |
| 6,388,043 B1 | 5/2002 | Langer et al. |
| 6,488,962 B1 | 12/2002 | Berner et al. |
| 6,579,301 B1 | 6/2003 | Bales et al. |
| 6,833,488 B2 | 12/2004 | Bucevschi et al. |
| 6,981,980 B2 | 1/2006 | Sampson et al. |
| 2004/0186502 A1* | 9/2004 | Sampson et al. .............. 606/191 |

(Continued)

FOREIGN PATENT DOCUMENTS

| | | |
|---|---|---|
| DE | 199 20 855 | 11/2000 |
| EP | 0 103 481 | 3/1984 |

(Continued)

OTHER PUBLICATIONS

International Search Report and Written Opinion, Corresponding to International Application No. PCT/US2008/087701, Mailed Mar. 10, 2010.

*Primary Examiner* — Katherine Dowe
(74) *Attorney, Agent, or Firm* — Greenlee Sullivan P.C.

(57) ABSTRACT

Disclosed is a swallowable self-expanding gastric space occupying device and related methods of making and using the device to control obesity. The device has a membrane through which gastric liquid can pass, wherein the membrane provides an enclosure volume separated from the gastric environment by the membrane. A plurality of self-expanding components is contained in the enclosure volume, so that the components expand in volume upon contact with the gastric fluid, thereby expanding the device from an unexpanded volume to an expanded volume. Composite membranes provide the ability to precisely control how and when the membrane degrades in the stomach, to release the self-expanding components from the enclosure and to ensure that the released pieces are sufficiently small to not obstruct any portion of the gastro-intestinal system.

25 Claims, 7 Drawing Sheets

U.S. PATENT DOCUMENTS

| | | |
|---|---|---|
| 2006/0058829 A1 | 3/2006 | Sampson et al. |
| 2007/0135831 A1 | 6/2007 | Burnett |
| 2007/0156248 A1* | 7/2007 | Marco et al. ................. 623/23.7 |
| 2007/0178160 A1 | 8/2007 | Burnett |
| 2008/0241094 A1 | 10/2008 | Burnett et al. |

FOREIGN PATENT DOCUMENTS

| | | |
|---|---|---|
| WO | WO 2005/084724 | 9/2005 |
| WO | WO 2007/109904 | 10/2007 |
| WO | WO 2007/115169 | 10/2007 |
| WO | WO 2009/049105 | 4/2009 |

* cited by examiner

SWALLOWABLE SELF-EXPANDING GASTRIC SPACE OCCUPYING DEVICE

CROSS-REFERENCE TO RELATED APPLICATIONS

This application claims the benefit of U.S. Provisional Application No. 61/015,269, filed Dec. 20, 2007.

BACKGROUND OF THE INVENTION

Disclosed are devices and methods related to treatment of obesity in animals or humans, and more particularly to reducing the appetite of a person being treated for obesity.

Obesity is a global disease that affects more than hundreds of millions people worldwide. Obesity causes or contributes to numerous serious medical conditions including type 2 diabetes, hypertension, cardiovascular disease, arthritis, sleep apnea, and certain types of cancer. Approximately 22 million adults in the U.S. are considered morbidly obese (BMI>35) and another 50 million are obese (BMI>30). Contributing to 120,000 deaths each year, obesity is considered the second leading cause of preventable death after smoking. In fact, obesity is more damaging to an individual's health than smoking and alcohol abuse.

The costs associated with obesity are enormous, with an estimated annual treatment cost exceeding $238 billion, of which roughly $100 billion is devoted to treating related health problems. Additionally, Americans spend $33 billion each year on weight-loss products and services. It is not commonly appreciated that individual weight-related costs can amount to more than $15,000 a year per person.

The most common treatments for obesity—diet, exercise and pharmacologic therapy—have poor long-term success rates. Obesity surgery, which entails surgical restriction of the size of the stomach with or without re-routing the intestine to cause malabsorption, has been proven to be the only effective means of achieving sustainable weight loss in obese patients. While the current surgical treatments for obesity are effective, they are expensive, major procedures involving irreversible reconstruction of gastrointestinal anatomy or surgically placed implants. Many patients who could benefit from those procedures forgo surgery due to the significant complications and long-term adverse event rates associated with those procedures.

Other approaches include intra gastric balloons, which are silicone balloons that are placed in the stomach and filled with liquid or gas. These balloons have been used for years to help people lose weight by limiting the amount of food that they can eat before filling the stomach and feeling full.

There are, however, numerous problems with those balloon devices including: They must be placed by a doctor using a catheter; they break down over time (6 months) and must be removed by a doctor with a catheter; the user has very little control over the amount of weight that is lost (e.g., the balloons are non-adjustable); once removed the user typically regains their weight; if they pop or break, they can occlude the digestive track leading to significant injury and additional surgery to correct.

The devices and methods disclosed herein solve the problem of a weight loss regimen that is safe, controllable, and without any surgical invention by providing a swallowable self-expanding gastric space occupying device made from base constituents that are sized to ensure that while the whole device cannot pass out of the stomach the constituents that make up the device can pass. Controlled degradation of the device in the stomach into base constituents that are smaller than the whole by forming a composite membrane ensures safe and efficient excretion of the device after a well-defined time in the gastric environment.

BRIEF SUMMARY OF THE INVENTION

Provided herein are devices that can be swallowed and that expands to occupy space within the stomach of an individual, thereby partially filling the stomach. The space occupied by the device physically limits the amount of food the individual can eat as well as creating a feeling of fullness that suppresses the individual's hunger. Accordingly, the device can assist an individual in managing and/or losing weight.

Advantages of various devices provided herein compared to conventional insertable or ingestible weight-loss devices include: (1) The device is swallowable like a pill by the user rather than placed by a doctor by a catheter; (2) The device can be taken in multiples to titrate the dosage to tailor the protocol to the individual's weight loss needs (e.g., many could be taken during the beginning of therapy with fewer taken later); (3) Materials may contain vitamins or pharmaceuticals; (4) The devices may be ingested continually over many years instead of just one application; (5) The device is simple in that it is self-expanding without any moving parts or valves; (6) The device can be tailored to provide a precise residence time in the stomach, after which controlled release of individual components ensures no obstructions will occur in the stomach or lower GI tract.

In an aspect, provided are membranes having at least two different materials (referred herein as a "composite membrane") having different degradation characteristics, such as degradation rate or time to mechanical failure within the stomach. This configuration provides breakdown and opening of the membrane in a controlled manner such that a single device degrades into a plurality of separate pieces, where each piece is sufficiently small to be passed out of the stomach and excreted by the patient without risk of complications related to obstruction.

In an aspect, the device is encapsulated, such as by an encapsulation material that is highly soluble so that the underlying device is rapidly exposed to the gastric environment after swallowing. Encapsulation is useful for ensuring the device does not expand in the esophagus and for facilitating handling and swallowing. Any material that is rapidly dissolved (e.g., in less than 10 minutes in the stomach), such as a starch, polysaccharide, or a gelatin capsule, may be used as the encapsulating material. The components that make up the device, and in particular the size of each individual component responsible for expanding the device's volume, ensure ingestion of the device is safe; even if the device ruptures, the device remnants can be simply excreted from the body without requiring additional time for degrading the remnants into smaller sizes.

In contrast with many conventional methodologies, the device is configured so that the maximum size of the self-expanding component is sufficiently small that each component can be passed from the stomach through the pyloric sphincter. Accordingly, the user or medical practitioner need not be worried about whether the component has appropriate biodegradation rates or that the device will obstruct the pyloric sphincter or the GI tract, such as due to premature rupture. In contrast, conventional devices are designed to provide a unitary expanded component that when expanded is so large that it must be broken down before it is capable of passing out of the stomach or being excreted. This means there can be a substantial risk of a GI block associated with those conventional balloon-type devices if they pop.

In an embodiment, provided is a swallowable self-expanding gastric space occupying device. In an aspect, the device has a membrane through which gastric liquid or fluid can pass, wherein the membrane provides an enclosure volume separated from the gastric environment by the membrane. In an aspect, the membrane is a composite, in that it may be made from two or more distinct materials that may be different chemically to provide a different rate of degradation and/or having a different geometric configuration to provide controlled opening of the membrane, thereby compromising the enclosure volume. Within the enclosure volume is a self-expanding component, such as a plurality of self-expanding components. The components are capable of expanding in volume upon contact with a gastric fluid, such as water for example, thereby expanding the device from an unexpanded volume to an expanded volume.

In an embodiment, any of the devices provided herein relate to a membrane capable of maintaining physical integrity in the gastric environment for a user-selected time period. In an aspect, physical integrity is maintained for 72 hours or greater. In an aspect, physical integrity is maintained for one week or longer, or for less than or equal to six months. Accordingly, as the device is designed to pass through the digestive system after a predetermined time, a sequence of the devices can be used for on the order of years to help an individual lose and maintain the weight loss. In an aspect, physical integrity is maintained for a time that is selected from a range that is greater than or equal to one week and less than or equal to two months. In an aspect, physical integrity is maintained for 72 hours or greater. In an aspect, physical integrity is maintained for a time that is greater than or equal to about one week and less than or equal to about two weeks. Such time lengths mean the device does not have to be taken with every meal or even every day and can, optionally, be incorporated with periodic weight management clinic visits.

The self-expanding components may be a powder, wherein each grain of the powder independently swells and expands in volume when contacted with a gastric fluid. In an aspect, the number of components is selected from a range that is greater than or equal to 20 pieces and less than or equal to about 10,000 pieces. In an aspect, the number of components is between about 30 and 40 pieces. In an aspect, the unexpanded volume of the component is about the size of a grain of sand, and when expanded expands to a volume that is about pea-sized. Examples of unexpanded component volume are a volume that is selected from a range that is between 100 $\mu m^3$ to 1.5 $mm^3$. In an aspect, the unexpanded components are selected and configured to minimize dead space within a capsule, thereby maximizing the device expansion ratio. Examples of expanded component volume are a volume that is selected from a range that is between 0.5 $cm^3$ to 3 $cm^3$.

In an aspect, the component is made from a material that is not substantially biodegradable, so that the component does not substantially degrade when exposed to normal gastric environment. In an aspect, the component comprises a hydrogel material and/or a shape memory polymer. Examples of hydrogels include, but are not limited to, polyacrylamide, polyethelene oxide, polyAMPS (2-acrylamido-2-methylpropanesulfonic acid), polyvinylalcohol, sodium polyacrylate and acrylates.

The membranes of any of the devices provided herein permit passage of gastric fluid without unwanted release of self-expanding components. Accordingly, the material from which the membrane is made may have appropriately sized or shaped openings or passages that permit fluid to pass, without allowing transit of materials whose size and shape corresponds to the size and shape of a self-expanding component in its unexpanded (or expanded) state. In an aspect the enclosure volume is formed by a membrane having at least a portion that is selected from the group consisting of a mesh, a porous layer, a woven fabric, a welded material, a sutured material, and a tied material.

In another embodiment, any of the devices have a membrane made from a first material and a second material, such as a composite membrane having two or more distinct structural materials. The first and second materials are operably connected to form the enclosure volume and the first material has a higher rate of decomposition in the gastric environment than the second material. The operable connection between the two materials provides a well-defined enclosure volume, but upon substantial degradation or dissolution of at least a portion of the first material, the enclosure opens, thereby releasing the self-expanding components from the enclosure. In an aspect, the first material has a higher rate of decomposition in the gastric environment than the second material so that the enclosure opens upon dissolution of at least a portion of the first material thereby releasing the components from the enclosure. Alternatively, the second material can be selected to have a higher degradation rate to provide dissolution of the second material before the first material.

In an aspect, the second material comprises a plurality of structural elements, wherein an individual structural element is connected to an adjacent structural element by the first material. In this aspect, dissolution or breakage of a portion of the first material results in breakdown of the membrane into a plurality of structural elements that are small enough to transit out of the stomach through the pyloric sphincter and be passed through the lower GI tract.

In an embodiment, the material in the membrane having a higher rate of decomposition in the gastric environment corresponds to a structure, such as a structure that is one or more of a suture, a weld and a tie.

In another aspect the membrane of any of the devices disclosed herein is formed into a geometric shape having invaginations or other slack in the membrane that is capable of accommodating expansion of the components as they expand. In an embodiment of this aspect, the device is encapsulated by an encapsulation layer that surrounds said membrane. In this embodiment, the invaginations or other slack in the membrane may be tightly packed together within the rigid encapsulation layer to facilitate swallowing by the patient. In another aspect, the membrane of the device is elastic so that expansion of the encapsulation volume is accommodated by stretching of the membrane without breaking the membrane. In another aspect the membrane has both slack and is elastic.

In an embodiment, any of the devices have expanded components with an individual volume that is sufficiently small to exit the stomach through the pyloric sphincter and that will not cause a small bowel obstruction. For example, the volume of an individual expanded component may correspond to about the size of a pea (e.g., about 0.5 cm in each length dimension), such as a volume that is less than a sphere having a diameter of about 0.5 cm or less, e.g., less than or equal to $4/3\pi(14)_3$ $cm^3$. Such a size ensures the component, even in an expanded state, can freely pass through the GI tract.

In an aspect, the device in an expanded state has an expanded volume that is greater than or equal to 20 $cm^3$ and a shape that prevents the device from passing out of the stomach through the pyloric sphincter. For example, the minimum cross-sectional area of the device can be selected to be greater than the maximum cross-sectional area that can pass through the pyloric sphincter. In an aspect, the maximum expanded state volume of the device is less than or equal to 250 $cm^3$. In an embodiment of this aspect, the membrane is configured, such as with a composite membrane, to provide release of the expanded components that can individually exit the stomach without causing obstruction anywhere in the GI tract.

In another embodiment, any of the devices presented herein have a ratio of expanded to unexpanded volume that is greater than or equal to 100 and less than or equal to 200. One advantage of the devices presented herein is that they may controllably break down into individual elements (e.g., expanded components, membrane pieces) whose size is much smaller than the whole, so that they may be rapidly released from the stomach and excreted from the body without any need for further degradation, either in the stomach or in the lower GI tract.

In an aspect, any of the devices presented herein have a membrane that maintains physical integrity in the stomach for at least one week or more. In this aspect, physical integrity refers to the ability of the membrane to prevent release of expanded components out of the enclosure volume.

In another aspect of the invention, provided are methods of making a weight loss device. In particular, the methods relate to providing a plurality of self-expanding components, wherein the components expand upon contact with a gastric fluid and the components do not substantially degrade when in contact with the gastric fluid. The components are enveloped with a membrane, wherein gastric fluid is capable of passing through the membrane to contact the components and the membrane is capable of accommodating expansion of said components without rupture. The membrane is configured to ensure the unexpanded as well as the expanded components do not pass through the membrane.

In an aspect, the membrane is substantially inelastic and the enveloping step is accomplished by providing invaginations in the enveloped membrane to accommodate volume expansion of the components upon contact with gastric fluid. "Substantially inelastic" refers to a material that when strained by about 5% undergoes a permanent deformation such that the material cannot relax back to its unstrained state. For example, the material may exceed its yield stress and fracture.

In an embodiment, the membrane, or a portion thereof, is made of a material that degrades or dissolves over time in the stomach, thereby releasing the components to the gastric environment.

In an aspect, the membrane is formed by operably connecting a first material with a second material, wherein the first material has a higher rate of degradation in a gastric environment than the second material. In this aspect, substantial degradation of the first material results in the plurality of self-expanding compounds being released from within the envelope to the gastric environment during use of the device.

In an embodiment, the operable connection between the materials relate to providing a plurality of structural elements made of the second material, wherein each of the structural elements has a size that is sufficiently small to pass from a gastric environment through a pyloric valve. The structural elements are connected to adjacent structural elements by the first material. Selective degradation of the first material results in release of the plurality of structural elements and self-expanding components to the gastric environment, wherein the structural elements and components are capable of passing through the GI tract without substantial degradation. "Selective degradation" refers to any means that results in the first material being structurally affected by degradation in the stomach, thereby compromising structural integrity of the enclosure volume. Various examples of such means are provided herein, ranging from providing different degradation rates (e.g., by varying cross-linking, for example) to geometric presentation or material location such as by ties, sutures, stitching, etc. that results in increased accessibility to the material by the gastric environment.

Also provided are methods of promoting weight loss in a patient using one or more of any of the devices disclosed herein. The method relates to positioning a plurality of self-expanding components in an internal volume formed by a membrane to make a self-expanding space occupying device. A patient swallows the device by oral ingestion so that the device is positioned in the patient's stomach. Gastric fluid then contacts the components as the gastric fluid can pass from the gastric environment through the membrane to the internal volume. This contact results in expansion of the components, thereby expanding the volume of the device in the gastric space to promote a feeling of fullness in said patient. As needed, additional devices may be swallowed to further increase the volume of occupied gastric space.

In another embodiment, the weight loss promotion method relates to devices wherein the membrane degrades in the gastric space. The membrane degradation releases the plurality of self-expanded components into the gastric space, wherein each of the self-expanded components has an expanded volume and shape configured to prevent a small-bowel obstruction. The self-expanded components are passed out of the patient body by travel through the gastrointestinal system. In an aspect, the components do not substantially degrade in the body and the shape and size of the components ensure the components, as well as any remnants of the device membrane, do not obstruct either the pyloric sphincter of the lower GI tract.

In another aspect, the invention relates to a swallowable self-expanding gastric space occupying device having a composite membrane through which gastric liquid can pass, wherein the membrane provides an enclosure volume separated from the gastric environment by the membrane. In this aspect, composite membrane refers to a membrane having a first and a second material each having different degradation characteristics. A different degradation characteristic results in one material undergoing a mechanical failure or dissolution before the other due to degradation in the gastric environment. Accordingly, the materials may have different degradation rates or a geometrical configuration such as layer thickness or accessibility to the gastric environment that results in one material failing before the other. A plurality of self-expanding components contained in the enclosure volume expands in volume upon contact with the gastric fluid, thereby expanding the device from an unexpanded volume to an expanded volume. The first and second membrane materials are operably connected to each other to provide the enclosure volume and controllable degradation of the membrane in the gastric environment.

The operable connection is by any means known in the art. For example, one material may be formed into one or more structures that at least partially preferentially degrade to provide designed breakdown of the membrane, thereby opening the enclosure volume to the gastric environment. In one embodiment, the structure is one or more sutures that attach adjacent separate pieces of the other material, such that upon degradation of the suture the membrane opens. In another embodiment, one material is a bond or a weld that over time degrades or loses adhesiveness such that the membrane opens. Another embodiment is provided by forming one material into a tie that encloses an opening in the membrane, and when the tie degrades the membrane opens. Another embodiment relates to coating a mesh with a material that at least partially fills the openings in the mesh and degradation of the coating over the openings facilitates release of the components. Alternatively, the mesh portion may degrade, resulting in release of the coating layer in pieces that were previously supported by the mesh material. In each of these embodiments, the membrane opening results in release of the self-expanding components and corresponding passage of the device remnants out of the patient through the GI tract without the need for any further degradation.

DETAILED DESCRIPTION OF THE INVENTION

Figure 1:
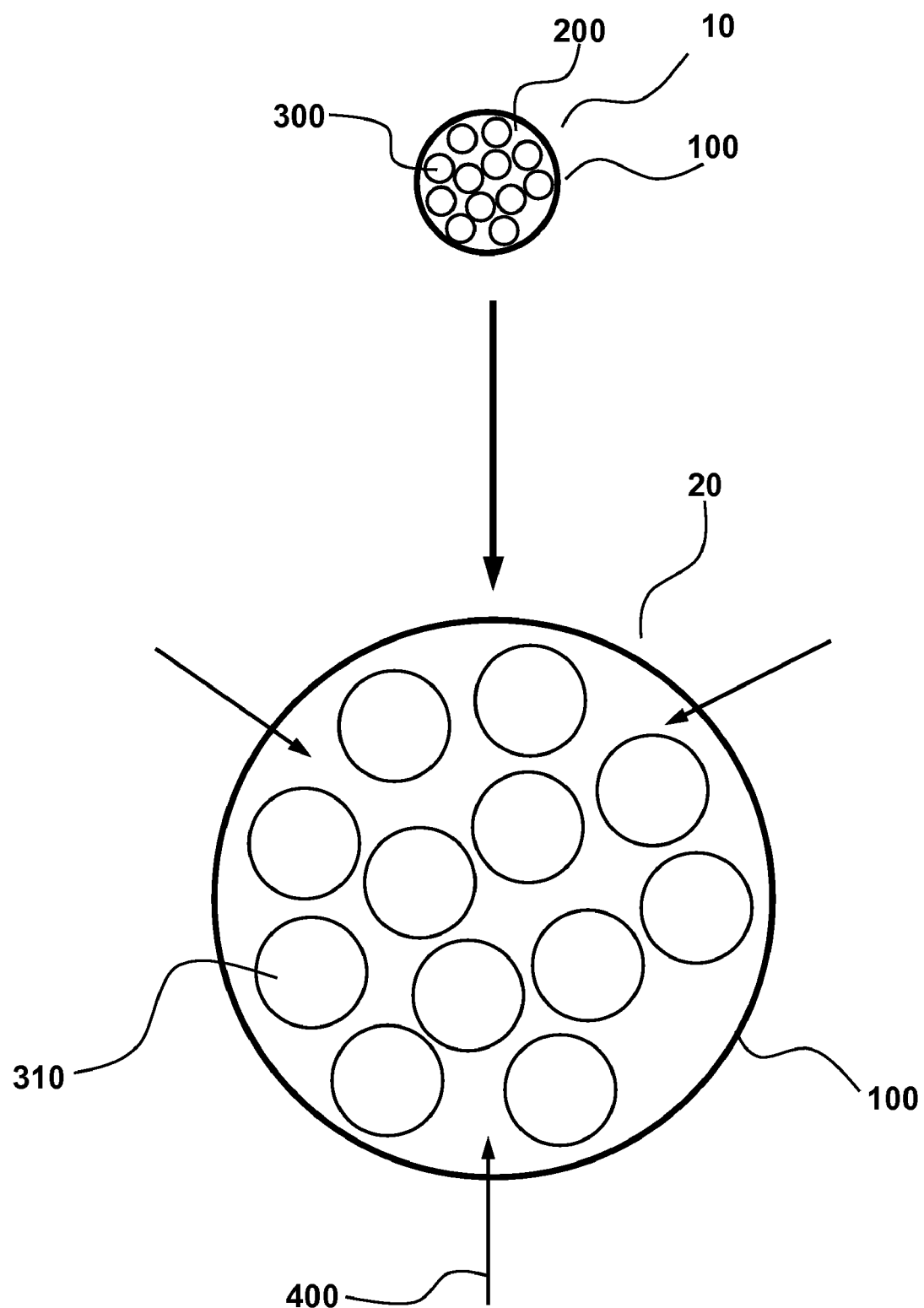
FIG. 1 is a schematic diagram of one embodiment of a self-expanding gastric space occupying device. A illustrates a device in its unexpanded state and B is a device in its expanded state after volume expansion of the space-expanding components.

"Swallowable" refers to a device having a volume and shape capable of, when swallowed by a patient, of transiting along the esophagus from the mouth to the stomach. To assist in swallowing, the device may be encapsulated, such as by a 000 capsule or smaller. For example, the capsule may comprise a hard gelatin capsule that rapidly degrades in the stomach to expose the encapsulated device. The capsule can be optionally cylindrical in shape and a volume sufficiently small to be swallowed without becoming trapped in the esophagus. For example, the volume can be less than or equal to about 1.4 cm$^3$, with an outer diameter that is less than about 1 cm. In an aspect, the minimum diameter of the capsule, or device that is not encapsulated, is smaller than the esophageal diameter, such as less than 1.5 cm or about 1 cm or less in diameter.

"Self-expanding" refers to the ability of a material to undergo a change in volume based on the material's inherent properties. For example, a material that when exposed to the gastric environment increases in volume. The exposure may be to one or more physical properties such as temperature, pH or liquid environment. Alternatively, the exposure may be tailored to a specific substance in the stomach or other part of the body, such as an enzyme. In one aspect, the expansion occurs by contact with gastric fluid in the stomach.

"Space occupying" refers to a material that remains substantially intact and physically occupies a defined volume within the stomach.

As used herein, "membrane" is used broadly to refer to a material formed to provide an enclosure that is capable of holding a plurality of self-expanding components within a defined enclosure volume. In an aspect, the membrane permits passage of gastric fluid from the gastric environment, across the membrane and through to the enclosure volume. Once in the enclosure volume the gastric fluid is capable of contacting the self-expanding components, thereby initiating volume expansion from an unexpanded volume to an expanded volume. Any means that permits passage of fluid across the membrane may be used. For example, the membrane may be an elastic form-fitting membrane having intimate contact with the self-expanding components on the inner surface of the membrane. Pores or other openings configured to ensure the smallest size components cannot exit from the enclosure, that permit passage of fluid may be incorporated into the membrane. The membrane may be made from a flexible and/or stretchable synthetic material. In one embodiment, the membrane is made from silicone, silicone elastomers, cellulose, cellulose acetate, cellophane, latex, polyurethane, PTFE, FEP, polylactic acid, polyglycolic acid, polyesters, polycaprolactone, and composites thereof. As required, the membrane may be formed to provide various structures such as meshes, pores, holes, passages, woven fabric, etc. that permit passage of gastric liquid but prevent release of self-expanding components contained within the enclosure volume. The membrane may be folded or collapsed to facilitate swallowing and expansion of the self-expanding components within the enclosure volume.

"Self-expanding component" refers to a material within the enclosure volume that is capable of undergoing a volume change in response to contact with gastric fluid, such as, for example, water. "Component" is used broadly herein to refer to any material or composite of materials that may undergo a change in volume in response to a physical stimulus or a plurality of physical stimuli. Examples of components include, but are not limited to, polymers that are hydrogels or shape memory polymers A membrane is said to have "physical integrity" if the membrane remains capable of maintaining the plurality of components within the enclosure. A membrane whose physical integrity has been compromised refers to the situation where a component has been released or has escaped from the enclosure defined by the membrane.

"Biodegradable" refers to a material that undergoes degradation within a biological system, and specifically one or more of the gastric, intestinal and digestive systems. A material's susceptibility to biodegradation can be controlled by chemical modification, such as increasing susceptibility to a material found in the surrounding environment (e.g., intestinal enzymes such as bile, lipases, etc.) or to pH. Although materials are generally susceptible to degradation when exposed to harsh conditions (such as in the gastric or digestive systems), some are more susceptible than others. A material that is "not substantially biodegradable" refers to a material that does not significantly dissolve, erode or otherwise decompose or degrade, and maintains overall physical integrity, such as a decrease in bulk material volume or mass that is less than 10%, for a user-specified time period. Examples of a time period are for at least one week, or at least three days. "Chemically inert" refers to a material that does not undergo a chemical reaction when inserted in the gastric, digestive or intestinal systems.

Examples of useful self-expanding components include polymeric formulations, hydrogels and composite materials thereof. Particularly useful polymers include hydrophilic polymers that swell upon absorbing water from gastric fluid, thereby expanding in volume or shape memory polymers.

Examples of suitable polymers for use in a self-expanding component include, but are not limited to, water-soluble polymers or co-polymers, e.g., polymers or copolymers capable of swelling upon contacting with water. Such polymers include, for example, polyvinyl alcohol, poly(ethyloxazoline), poly(2-hydroxy ethylacrylate), poly(2-hydroxy ethylmethacrylate), polyacrylic acid, polysaccharides, proteins, polynucleic acids, and the like. In one embodiment, the polymers are polyvinylacetate-polyvinylalcohol copolymers, poly(2-hydroxyethyl acrylate) and copolymers, poly(ethyloxazoline) and copolymers, or poly(2-hydroxyethylmethacrylate) and copolymers.

As used herein, the term "polysaccharides" includes polysaccharides, polysaccharoses, sugars, and the like. Exemplary polysaccharides include starch, sodium starch glycolate, alginic acid, cellulose, carboxymethylcellulose, hydroxyethylcellulose, hydropropylcellulose, hydroxypropylmethylcellulose, ethylcellulose, carageenan, chitosan, chondroitin sulfate, heparin, hyaluronic acid, pectinic acid, chitosan, hyaluronic acid, xanthan gum, starch, maltodextrins, corn syrup, alginates, and the like. Various proteins may be used including, but not limited to, water soluble proteins, e.g., albumin, gelatin, and the like.

According to one embodiment of the present invention, the oral dosage form or polymeric formulation of the present invention includes a polymer that is biocompatible and/or pH sensitive, e.g., sensitive to intestinal pH. Such oral dosage form or polymeric formulation typically includes a dehydrated combination of a biocompatible polymer, e.g., an alginate and a solubilizer/stabilization agent, e.g., xanthan gum, propylene glycol alginate, and the like (to allow for maintenance of a firm solid polymer within the gastric environment) covered with an acid-sensitive coating (e.g., a gelatin). Alginate itself precipitates to a certain degree in the acidic environment of the stomach and so in an optional embodiment an additional component is provided in order to prevent precipitation. In one embodiment, the additional component is propylene glycol alginate. In another embodiment, the solubilizer/stabilization agent is sensitive to intestinal pH. For example, propylene glycol alginate forms a solid in the stomach but becomes viscous at intestinal pH. Typically, about half of the polymer of alginate with propylene glycol alginate is degraded after 3 to 4 hours at intestinal pH. Alternatively, in embodiments where the self-expanding component is designed to yield an expanded volume that is sufficiently small to pass through the intestines and bowels, the component need not be made from a material capable of degrading.

According to another embodiment, the polymers described herein are cross-linked. Cross-linking is one means for controlling the rate of degradation, with higher cross-linking resulting in a lower degradation rates. Cross-linking can be achieved either through a covalent cross-linker or non-covalent cross-linker. Examples of covalent cross-linkers include, but are not limited to, homobifunctional cross-linkers with reactive molecules of diglycidyl ethers, substituted and unsubstituted diN-hydroxy succinimides (NHS), diisocyanates, diacids, diesters, diacid chlorides, dimaleimides, diacrylates, and the like. Heterobifunctional cross-linkers can also be utilized. Heterobifunctional cross-linkers generally include molecules that contain different functional groups to accomplish the cross-linking, for example, combining NHS and maleimide, an acid and ester, etc.

Non-covalent cross-linkers, e.g., based on ionic, hydrogen bonding and other intramolecular associations are also contemplated for use in the practice of the invention. Examples of non-covalent cross-linkers include, but are not limited to, chitosan/polyacrylic acid, polyacrylic acid/polyethylene glycol (at low pH), polyacrylic acid copolymers and hydroxyl containing polymers, polymers containing carboxylic acid pendant groups, pluronics (ethylene oxide-propylene oxide-ethylene oxide (EO-PO-EO) triblock copolymers), metal cross-linked polymers, ionomers, and the like. The non-covalent cross-linkers can be based on hydrophobic associations. Such non-covalent cross-linkers can be any suitable system that demonstrates lower critical association temperatures including, without any limitation, pluronics (triblock copolymers of ethylene oxide and propylene oxide structured as EO-PO-EO), which can form gels at elevated temperatures such as body temperature and convert to a soluble form at a lower temperature such as room temperature.

In one embodiment, the cross-linker contains one or more hydrolysable groups. In another embodiment, the cross-linker is susceptible to hydrolysis, e.g., either by chemical means or by biological means such as enzyme catalyzed hydrolysis. In yet another embodiment, the cross-linker is a polymer or copolymer of lactic acid, glycolic acid, trimethylene carbonate, caprolactone, or any other hydrolysable esters. In still another embodiment, the cross-linker includes a linker between the cross-linking functionalities that renders the ultimate cross-linked polymer a degradation susceptibility towards an intestinal enzyme, e.g., susceptibility to degradation by an intestinal enzyme. These types of cross-linkers typically include basic sensitive groups or $C_{12}$-$C_{22}$ aliphatic unsaturated hydrocarbon linkers, since an intestinal enzyme such as a lipase recognizes fatty acid type structures. In some embodiments, these linkers include diacids that form alpha-omega ester linkages between polymer chains, thereby cross-linking the polymer chains. In addition, oligoesters having alternating PEG spacers can be utilized. Indeed, PEG chains or other hydrophilic spacers can be incorporated into the cross-linkers to control hydrophilicity and swelling of the polymers from which the self-expanding are, at least in part, formed.

According to another embodiment, the polymer can be any polymer that degrades faster in an environment with an intestinal pH, such as a pH of about 8. In contrast, the component does not significantly degrade in the gastric environment where the pH is typically acidic (e.g., pH between about 2 and 3). In one embodiment, the polymer is a cross-linked hydrogel formulation held together by physical cross-links between acid groups and ether oxygens. Examples of acid containing polymers include carboxymethylcellulose, agarose, polyacrylic acid and copolymers, etc. Polymers containing ether oxygens include, for example, any PEGs (branched or linear), any PEG copolymers including, without any limitation, pluronics, polysaccharides, starches, etc.

In another embodiment, the polymer of the present invention includes any polymer containing pendant acid groups or chemically hydrolysable groups. For example, polymers containing one or more pendant acid groups, e.g., carboxymethylcellulose, agarose, polyacrylic acid and copolymers etc. and/or chemically hydrolysable groups, e.g., anhydrides, ketals, acetals, and esters can be covalently cross-linked. In general, as the pH increases in an environment the hydrolyzability of the ester groups in these polymers can increase due to their increased accessibility caused by the polymeric swelling.

In an embodiment, the component is made from a shape memory polymer. Any shape memory polymer known in the art and composites thereof can be used so long as the polymer expands when positioned within the gastric environment. Examples of shape memory polymers include, but is not limited to, those disclosed in U.S. Pat. Nos. 6,160,084 and 6,388,043. Shape memory polymers are commonly designed to change shape in response to changes in temperature. Shape memory polymers can, however, be designed to change shape in response to other physical parameter changes such as in response to application of light, changes in ionic concentration, changes in pH, electric field, magnetic field and/or ultrasound. The temporary shape in these polymers can be fixed by the covalent crosslinks. The shape memory polymeric composition can include at least one hard segment and at least one soft segment or multiple soft segments that are covalently crosslinked, wherein at least two of the segments are linked via a functional group which is cleavable when implanted in the stomach and brought into contact with the gastric environment or fluids from the gastric environment.

In an embodiment, the component is made from a material that is a hydrogel. Various hydrogel materials and composites thereof are generally known in the art, including superporous hydrogels, as discussed in, for example, U.S. Pat. No. 6,271,278, specifically incorporated by reference for the expandable hydrogel compositions and methods of making same. "Hydrogel" refers to a crosslinked polymer network that is insoluble in water and that swells in the presence of excess water. The devices and methods disclosed herein are compatible with a range of hydrogel materials known in the art. Any hydrogel having appropriate characteristics related to swelling ratio, swell rate, biodegradability (or lack thereof) for the application of interest may be incorporated into the self-expanding component. For example, non-porous, porous or a composite of non-porous and porous hydrogels may be used in the self-expanding component.

The hydrogel may range from a compact gel to a loose polymer network. Appropriate hydrogel materials are made as known in the art, such as by solution polymerization techniques (see, e.g., U.S. Pat. No. 6,271,278), where hydrogel characteristics are controlled by selection of monomer type, amount of diluent in the monomer mixture, and the amount of crosslinking agent. For example, pore size in the hydrogel can be controlled, with higher pore sizes generally providing more rapid swelling rates. In an aspect, self-expanding components having fast swelling rates are desirable for ensuring the device rapidly expands after entering the stomach, thereby ensuring it does not pass out of the stomach through the pyloric sphincter. In an aspect, the self-expanding component swells to at least 30% of its maximum volume within 15 minutes after entering the stomach, or a volume that is sufficiently large that the device cannot exit the stomach.

Some examples of hydrogels that may be used herein include, but are not limited to, those disclosed in U.S. Pat. Nos. 5,750,585, 6,271,278 and 5,750,585, for example. Specific examples include, but are not limited to, poly(N-isopropylpolyacrylamide) and crosslinked hydroxypropylcellulose. Suitable hydrophilic monomers/polymers for making hydrogels are known in the art and include those described in U.S. Pat. Nos. 4,178,361 and 3,551,556, such as poly(acrylic acid) (PAA), polyacrylamide (PAM), polyvinylpyrrolidone (PVP), hydroxyethyl methacrylate (HEMA), poly(2-hydroxyethyl methacrylate) (PHEMA), and poly(2-hydroxypropyl methacrylate) (PHPMA). Hydrogels may also be formed from solutions of two or more different monomer species to form hydrogel co-polymers, such as from one or more of acrylamide, acrylic acid, vinylpyrrolidone, 2-hydroxyethyl methacrylated and 2 hydroxypropyl methacrylate. In an aspect, the hydrogel is dried or at least partially dehydrated and provided within an enclosure formed by the membrane. Optionally, the membrane is encapsulated by a bioerodible material.

"Operably connected" refers to a configuration between two materials such that a functional enclosure is formed for containing the plurality of self-expanding device components, but that preferential degradation of one of the components results in the release of the components from the enclosure. The operable connection is by any means known in the art. For example, one material may be a "tied material" that ties the second material closed to form an enclosure. Alternatively, one material may form a bond or weld to particular regions of the other material, thereby forming the enclosure, which is referred to as a "welded material". Similarly, one material may be sutured together by a second material referred to as a "sutured material".

A "composite membrane" refers to a membrane that is formed from two or more different materials. A material is different if it has different physical properties, such as rate of degradation in the gastric environment. Accordingly, materials made of the same constituent materials are considered different if they have different chemical composition, such as a different amount of cross-linking that provides different degradation characteristics, such as degradation rate. Similarly, materials are considered different if they have different constituents that in turn lead to different degradation characteristics. Alternatively, a first material and a second material can be different based on a geometrical shape or a position that results in preferential degradation of one material compared to the other. This can be achieved in any number of ways, such as making dimensionally smaller (e.g., thinner) material that will structurally break sooner than thicker materials, exposing a greater surface area to the substances responsible for degrading in key structural locations, and/or coating or protecting specific locations with a mask or protective layer.

Examples of shaped materials that provide preferential breakdown or degradation include sutures, ties and welds. Each of those structures has key locations that are relatively thin, thereby resulting in specific break regions when exposed to the gastric environment. For example, sutures and ties are relatively thin and have regions exposed to the gastric environment. Welds or bonds can also be thin, and be formed at edge regions that are quickly exposed to the gastric environment. In this manner, the structural degradation and resultant break in the material results in an opening in the other material to which the structure is operably connected, thereby releasing contents within the enclosure to the gastric environment. Similarly, the operable connection may facilitate the first material being released into a plurality of individual structural elements, each sufficiently small to be passed by the GI system. In contrast, the structural elements operably connected to each other by a different material are too big when connected together to pass out of the stomach.

One important aspect of the membrane is the ability to accommodate an expansion of the components in the enclosure without rupture. This is accomplished in any manner of ways. For example, the membrane may be elastic. "Elastic" refers to a material that is capable of undergoing significant strain or stretch without fracture or permanent material breakdown. Alternatively, the membrane may be relatively rigid but may be constructed to have slack that can accommodate increase in the volume of the self-expanding components. One example is by forming a membrane with invaginations that provides the ability for the membrane to deform without experiencing significant strain or stress. Similarly, such as with a membrane that is a fabric, the membrane may be folded in on itself so that the enclosure is much larger than the unexpanded components, and that upon expansion the fabric can accommodate the expansion without significant strain or stress. In this aspect, an encapsulation layer can surround the membrane, thereby constraining the outer membrane of the device to a shape and/or volume that is conducive to swallowing. Once the encapsulation layer dissolves in the stomach, the membrane is able to unfold and accommodate expansion of the enclosure volume as the self-expanding components increase in volume.

In the aspect where the membrane contains pores or mesh through which gastric fluid can pass, the openings are configured to ensure the self-expanding components cannot pass through the membrane. For example, the openings are smaller than the minimum cross-sectional area of the component and/or the passages are tortuous. A "tortuous passage" refers to a passage that may be sufficiently large for a component to traverse, but is shaped in such a manner as to substantially prevent the components from entering the gastric environment via the passage. When the membrane has opened, after degradation of one or more materials making up the membrane, the expanded components are released to the gastric environment. Accordingly, in an aspect each of the expanded components has a shape and volume that permits passage of the component through the GI tract, including the pyloric sphincter, even for a component that does not substantially degrade.

"Enveloping" refers to forming the membrane so as to provide in inner facing surface that defines a volume for holding a self-expanding membrane. "Encapsulating" refers to providing an encapsulation layer that covers a device of the present invention.

A material may be incorporated that is sensitive to a specific enzyme, thereby facilitating localized degradation. For example, lipids or carbohydrates may be incorporated into a polymer, wherein the incorporated material is more susceptible to chemical breakdown by an enzyme. These degradation-sensitive materials may be strategically positioned in the membrane to facilitate controlled membrane rupture or membrane breakdown into precisely-sized pieces that can be easily excreted from the body.

The invention may be further understood by the following non-limiting examples. All references cited herein are hereby incorporated by reference to the extent not inconsistent with the disclosure herewith. Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

Devices and related methods disclosed herein relate to a device that is sufficiently small to swallow, but that subsequently expands in volume when in the stomach. In particular, the volume expansion relates to expansion of one or more self-expanding components enclosed within a membrane that is permeable to gastric fluid. The expansion is sufficiently large so that the expanded device cannot escape the stomach. The individual components, in contrast, are sufficiently small to escape the stomach and, furthermore, will not cause a blockage in any portion of the GI tract. In particular, the membrane is optionally constructed so that it degrades over time to release the self-expanding components to the stomach where they are free to transit the GI tract. In addition, the membrane may be a composite membrane made from a plurality of materials wherein the degradation of one material results in release of the other material in distinct individual structural elements whose size is smaller than the whole and may have a size sufficiently small to transit the GI tract without blockage.

FIG. 1 is one example of a swallowable self-expanding gastric space occupying device 10. A membrane 100 is formed to have an inner surface that defines and enclosure volume 200. Volume 200 contains self-expanding component 300. FIG. 1A illustrates the device in unexpanded state 10. FIG. 1B illustrates device in its expanded state 20. In particular, self-expanding components have expanded from an unexpanded 300 to an expanded volume 310 by passage of gastric fluid 400 through the membrane 100, thereby increasing the volume of device 10. In an aspect, there is a plurality of self-expanding components.

Figure 2:
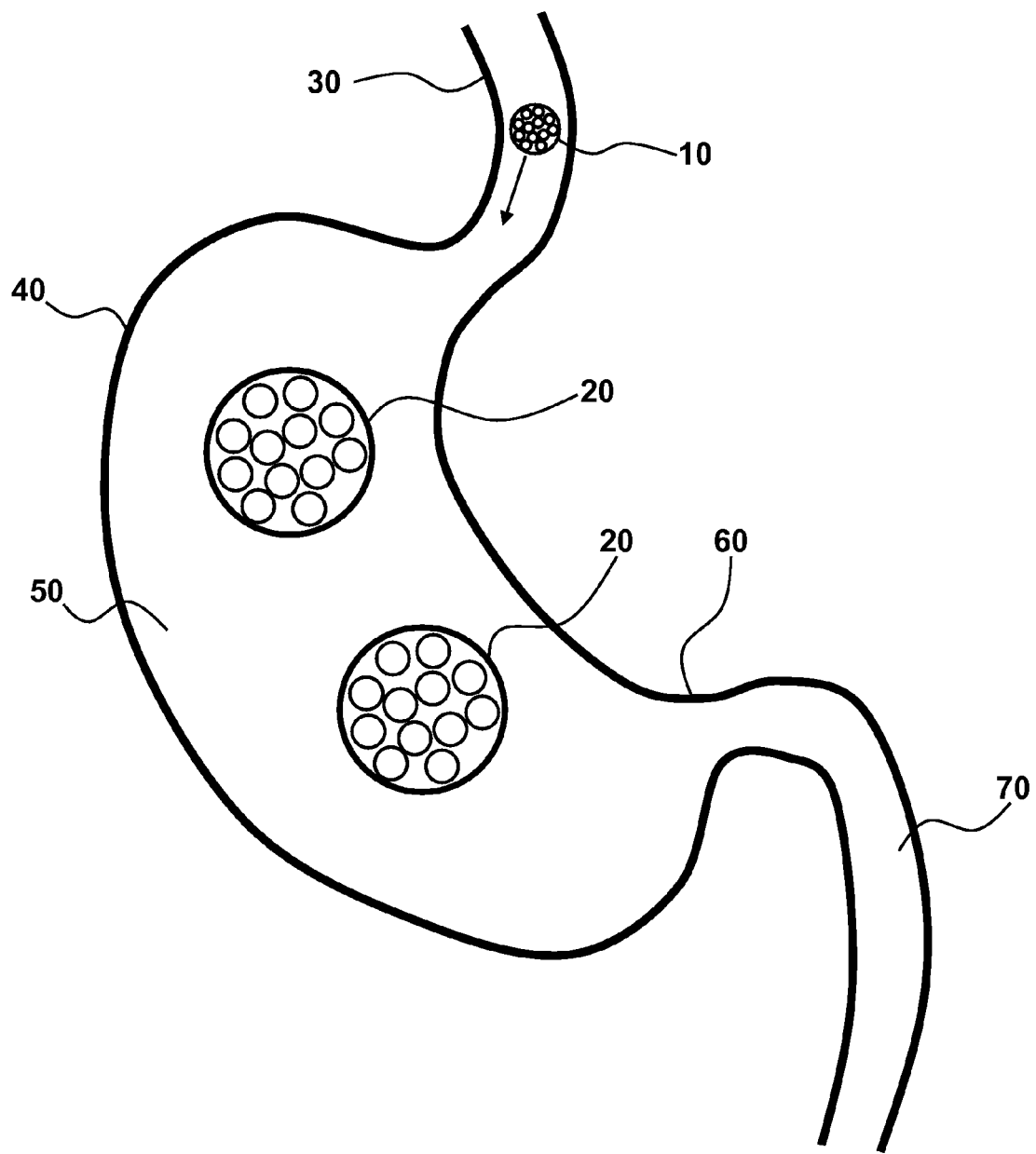
FIG. 2 schematically illustrates a device transiting the esophagus on its way to the stomach and two devices in the gastric space that have expanded in the stomach.

FIG. 2 illustrates unexpanded device 10 transiting the esophagus 30 after being swallowed by the patient. In addition, shown are two devices residing within the stomach 40, and specifically in the gastric space or environment 50, in their expanded state 20. In an aspect, provided are methods wherein a single device resides in the stomach. In another aspect, provided are methods wherein more than one device resides in the stomach. The expanded device 20 is too large to pass into the lower GI tract 70 through pyloric sphincter 60, even under peristaltic contraction.

Figure 3:
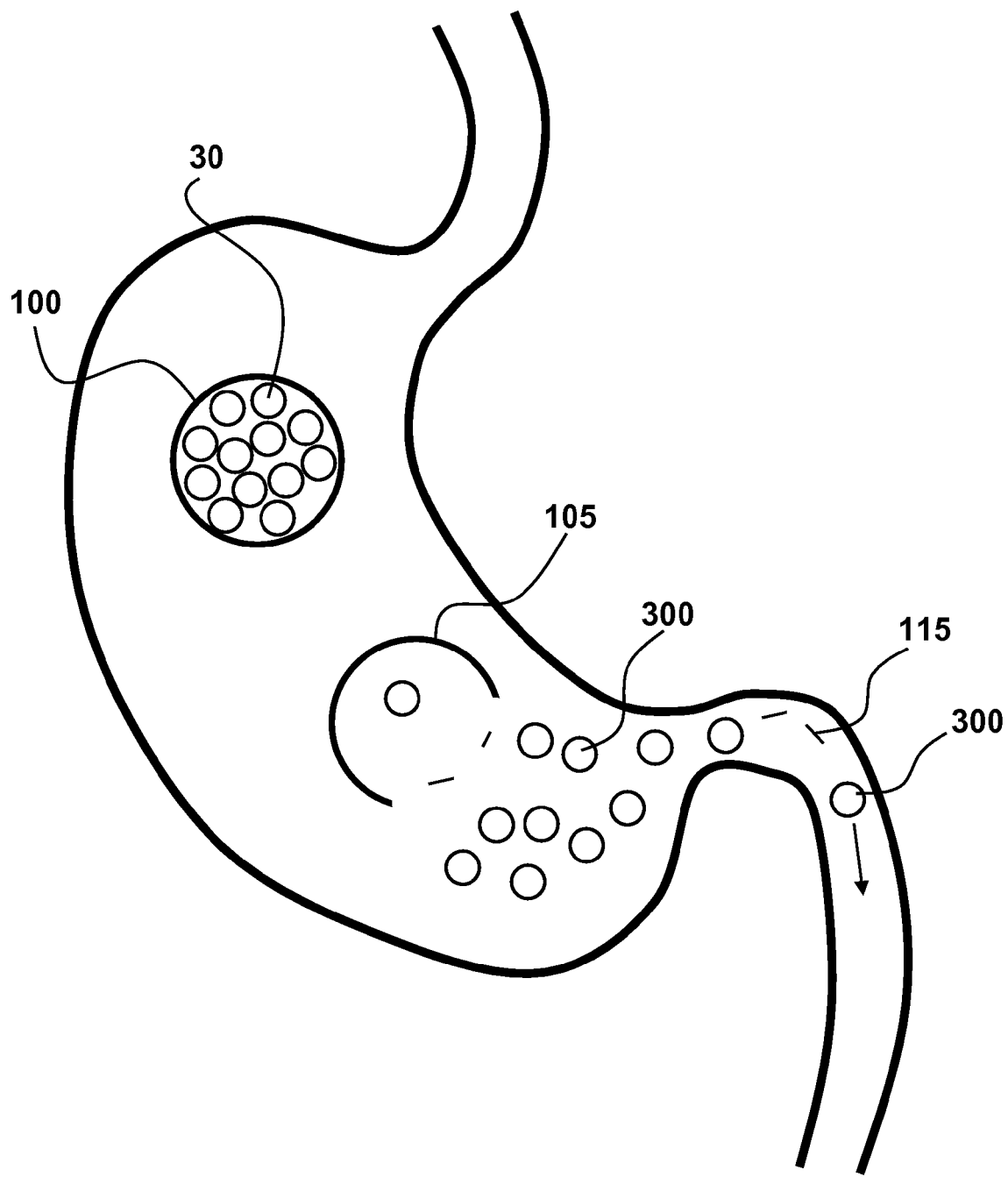
FIG. 3 illustrates that after a certain residence time, a device membrane or a select portion thereof degrades, resulting in release of the expanded components from within the device enclosure. Portions of a device that do not degrade are designed to be sufficiently small to permit passage from the stomach to the lower portion of the gastrointestinal (GI) tract where they are then excreted from the body.

After a certain time in the stomach, generally ranging on the order of a week or more, or more than about 3 days, the device 20, and specifically the membrane 100, begins to degrade (FIG. 3), resulting in a compromised membrane 105 that can no longer restrain components 300. As discussed, the decay may be preferentially confined to specific regions of the membrane 100, such as regions corresponding to a material having a higher etch or degradation rate within the stomach, resulting in release of the self-expanding component 300 and membrane structural elements 115 into the gastric environment. Each of the device constituents 115 and 300 are sufficiently small to pass through the GI system and be excreted from the body. Alternatively, one or both of structure 115 and 300 may also substantially degrade, resulting in further reduction of size, shape and/or volume to facilitate transit. As needed, additional devices 10 may be swallowed by the patient.

Figure 4:
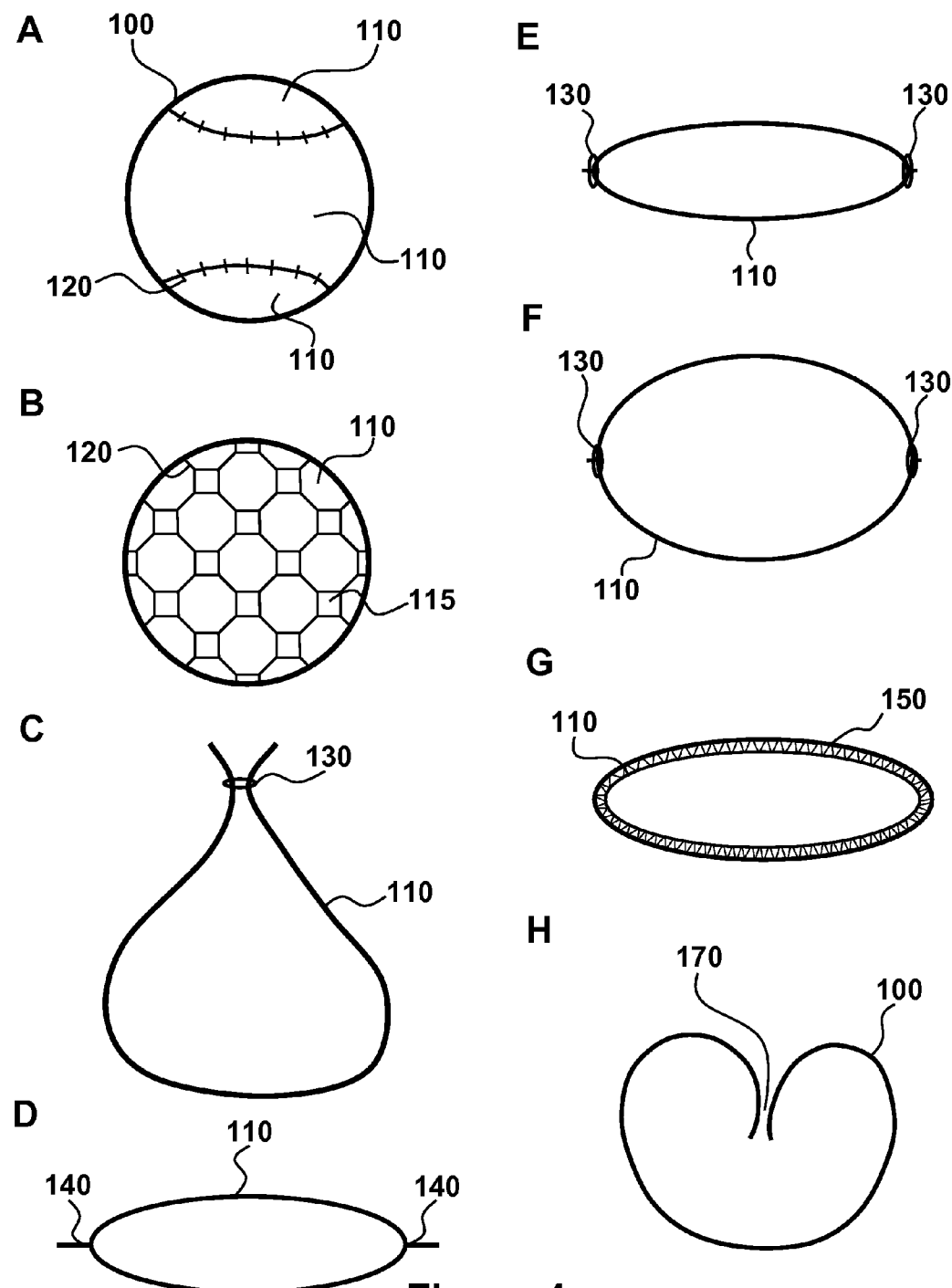
FIG. 4 provides schematic illustration of various membrane embodiments, including portions of the membrane made from a material that is formed into: A sutures; B structural elements; C, E, F ties; D welds or bonds; G stitches; and H tortuous passage.
Figure 5:
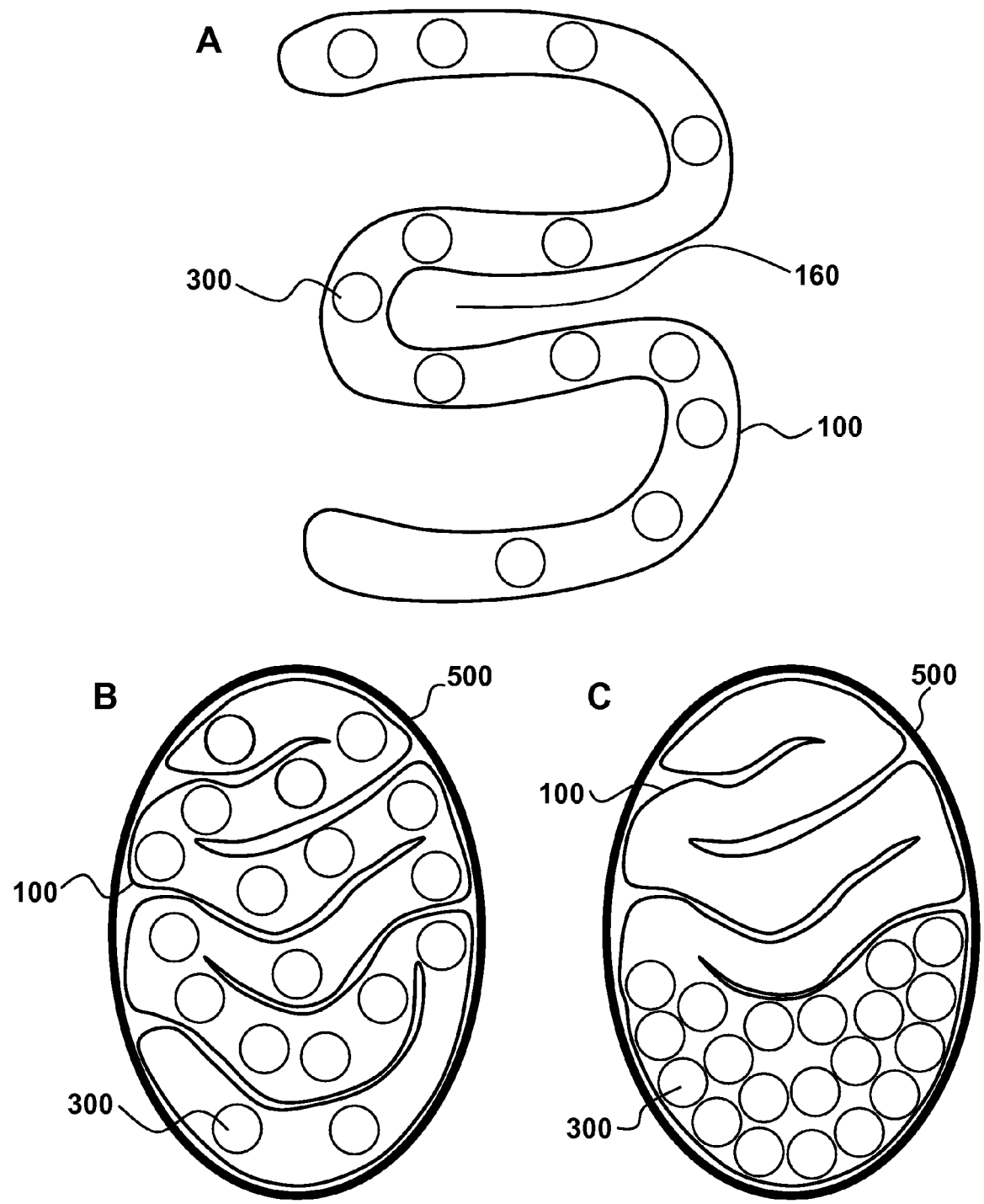
FIG. 5A illustrates an embodiment where the membrane has invaginations or folds that can accommodate expansion of the enclosure volume. B illustrates encapsulation of a membrane capable of folding or having invaginations with an encapsulation layer to facilitate swallowing of the device and subsequent travel along the esophagus. C illustrates another encapsulation embodiment.

The device may use various membrane compositions and shapes. Exemplary embodiments are provided in FIGS. 4-9. FIG. 4 summarizes how different materials, such as materials having different decomposition rates in the gastric environment, may be operably connected to provide for controlled release of components contained in enclosure volume. FIG. 4A illustrates a first material 110 and a second material 120 operably connected, wherein the second material is shaped and positioned in the membrane as a suture with a resultant degradation rate that results in breakage of suture 120 before material 110 degrades. In an aspect, the first and second materials may actually be equivalent, but that the shape of the second material 120 (e.g., thin and long) results in the second material breaking before the first material. As second material 120 degrades, breakage results in an opening of first material 110, thereby opening the enclosure volume so that the contents in the enclosure volume is released to the gastric environment (see, e.g., FIG. 3).

FIG. 4B illustrates the embodiment where the membrane comprises three separate material elements, such as three materials having different degradation rates in the stomach. In this example, first material 110 and structural elements 115 are connected via a second material 120 that may, for example, correspond to sutures, stitches, bonds, welds, etc. In an aspect, structural elements 115 may be relatively inert or resistant to degradation, but are sized sufficiently small so that they pass through the GI tract. In an aspect, portions of the membrane such as material 110 may also degrade in the stomach or the GI tract as desired, such as by releasing into portions whose surface area accessibility for degradation is higher after release than before release.

In another aspect, a second material may be formed into a tie 130 (FIGS. 4C, E and F) that functions to close an otherwise open first material 110. Various configurations and number of openings to be tied or sealed are provided, with examples of one and two opening systems summarized. Another example (FIG. 4D) is a material provided as a bond or weld 140 that seals an opening in a membrane formed from first material 110. FIG. 4G illustrates an example where first material 110 is sewn together with a second material 150 that are stitches. Stitches refer to continuous structures, in contrast to sutures where each suture is a stand-alone structure. One common element for each of the configurations in FIG. 4 is that one of the materials dissolves (or, more precisely, undergoes a structure failure) faster than another material from which the membrane is made, thereby resulting in an opening and subsequent release of self-expanding components 300 (see FIGS. 1-3) that can then pass from the stomach through the lower GI tract. An example of a tortuous passage 170 that can be used for passage of gastric liquid while at least substantially preventing premature release of components to the gastric environment is provided in FIG. 4H.

Optionally, membrane 100 is elastic to accommodate volume changes of the enclosure as the self-expanding components 300 expand. The membrane, however, can be configured to permit volume expansion without being elastic. For example, as shown in FIG. 5A, the membrane may have folds or invaginations 160 that permits the volume to change without exerting substantial strain on the membrane wall. For example, flexible woven fibers or fabrics can be packed within an encapsulation layer 500 as shown in FIG. 5B to facilitate swallowing. The encapsulation layer can rapidly dissolve in the stomach and the membrane unfolds to accommodate expansion of self-expanding components 300. FIG. 5C indicates the enclosure volume may be formed into one region containing the self-expanding components and a second region having slack for accommodating increase in the enclosure volume as the components expand.

Figure 6:
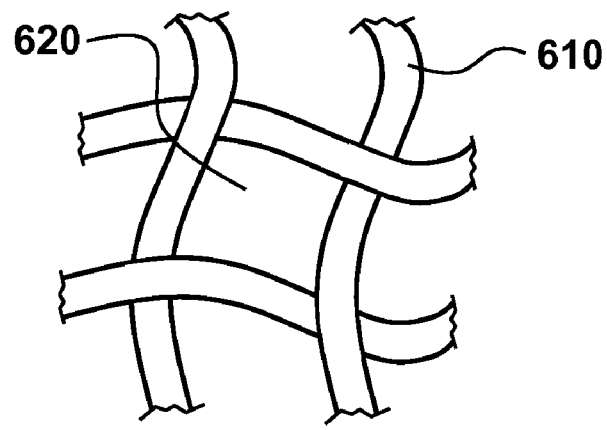
FIG. 6 is a schematic close-up of an embodiment where the membrane comprises a woven fabric or mesh.

At least a portion of the membrane is designed to permit passage of a liquid without release of self-expanding component (either unexpanded or expanded). Examples of materials include, but are not limited to, materials that are porous, mesh or of woven fabric. FIG. 6 illustrates a membrane where a first material is formed into a mesh or made from a woven fabric 610. The fabric or mesh 610 can be coated or dipped with a second material 620, such that the majority of the openings between mesh fabric material 610 is filled. Materials 610 and 620 can dissolve (e.g., degrade) at different times so that after a user-selected time, an opening in the membrane becomes large enough to release the self-expanding components. For example, material 620 may be a material that does not degrade or dissolve in the stomach, such as, for example a highly cross-linked polymer, a silicone-based material, or other inert material as known in the art including, but not limited to, fats, waxes, carbohydrate polymers (poly and oligosaccharides). In that situation, the dissolution of 610 results in release of material 620 from the membrane, loss of membrane integrity, release of self-expanding components 300 and movement out of the stomach and through the lower GI tract.

Alternatively, material 620 may be highly or rapidly degradable in the stomach. In that situation, degradation of 620 reveals holes in the membrane 100 sufficiently large for self-expanding components 300 to escape. Further exposure of material 610 upon dissolution of 620 may help facilitate further degradation or collapse of material 610 in the stomach and/or lower GI tract. In an aspect, one surface of fabric 610 is dipped or coated in material 620. In an aspect, the entire surface of fabric 610 is dipped or coated with material 620.

Figure 7:
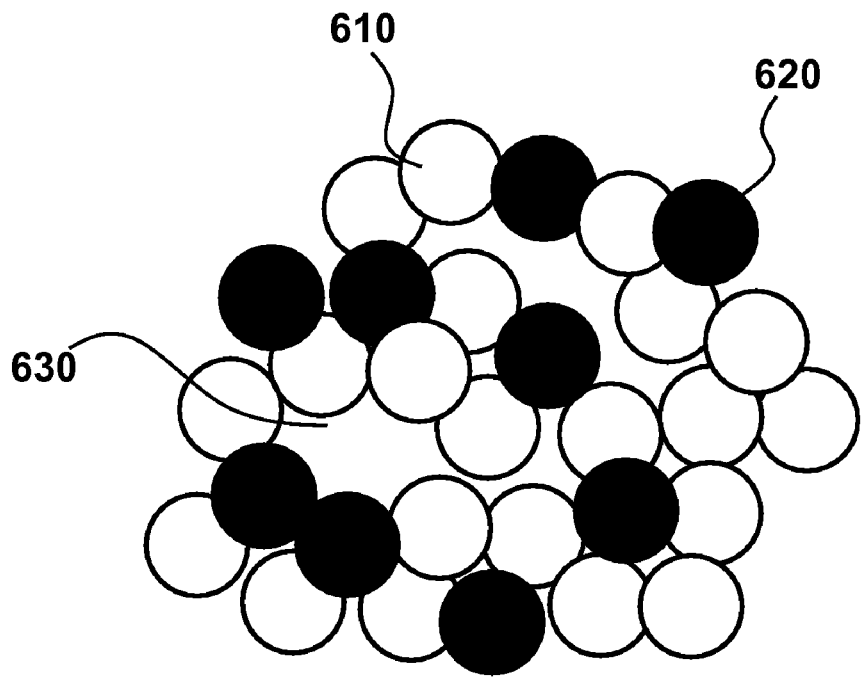
FIG. 7 illustrates an embodiment where the membrane is made from individual pieces, including from subsets comprising different populations of material, and bonded to form sheets optionally having holes, gaps or pores between the materials to facilitate entry of gastric fluid without release of self-expanding components.

In another aspect, the membrane 100 is formed from distinct elements that are bonded together to form sheets. An embodiment is shown in FIG. 7 where a first material 610 is bonded with a second material 620. Further provided are optional holes, gaps or pores 630 that permit passage of gastric fluid but are too small for passage of self-expanding components out of the enclosure volume. As one of material 610 or 620 degrades, the holes expand and/or portions the membrane are released, thereby permitting release of the self-expanding components. The different materials may be arranged randomly or in an ordered pattern with respect to each other.

Figure 8:
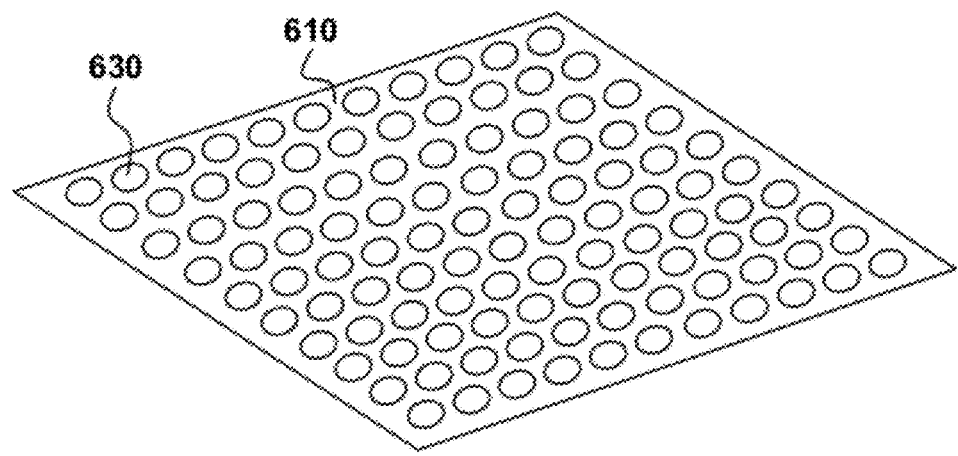
FIG. 8 illustrates a membrane having pores or passages formed by perforating the membrane with holes.

Another embodiment of membrane 100 is shown in FIG. 8, where a plurality of pores 630 is formed in the membrane material 610, such as by perforating the layer material. The size of pores are large enough to permit passage of a gastric fluid or liquid, but small enough to ensure that unexpanded component 300 cannot be released from the enclosure volume.

Figure 9A:
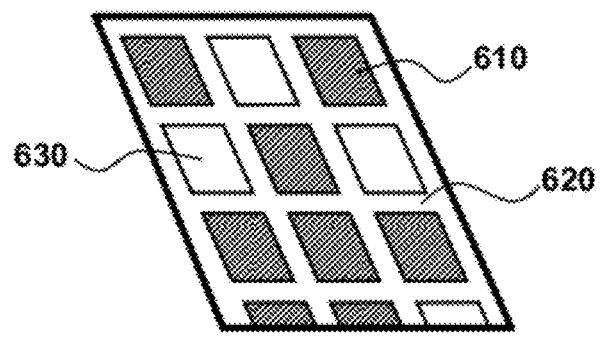
FIG. 9A is a multilayered membrane made from materials having different etch characteristics. B is a cross-section view of the membrane shown in A.
Figure 9B:
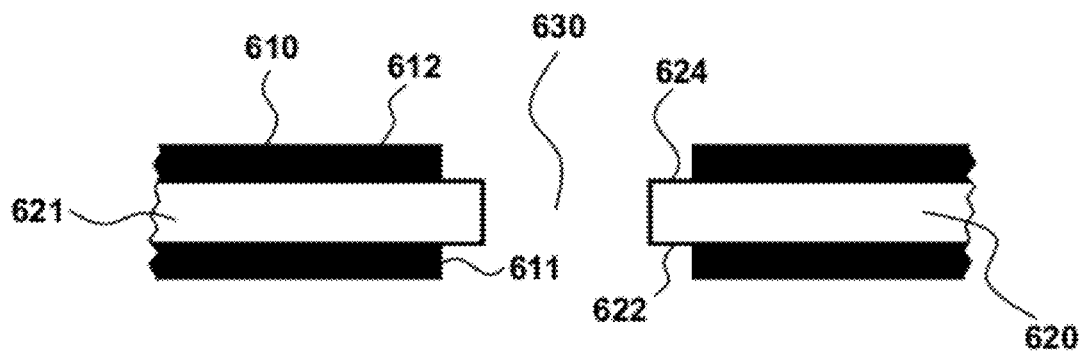

FIG. 9 illustrates an embodiment where the membrane comprises a multi-layer structure. A sheet of material 620 having an inner-facing surface 622 and an outer-facing surface 624 is covered with another material 610, such as material 610 having a lower degradation rate (or no degradation) in the stomach than material 620. FIG. 9B illustrates an embodiment where the membrane comprises three layers, with the sheet of first material 620 forming a middle layer 621, and the second material 610 forming an inner layer 611 and an outer layer 612 that at least partially coats the inner-facing 622 and outer-facing 624 surfaces of the sheet of first material 620. Optionally, provided are holes 630 as necessary to facilitate liquid diffusion across the membrane. In this aspect, material 610 provides structure and material 620 dissolves away. Multilayer configurations provides additional controllable degradation characteristics, where a more degradation resistant material 610 functions as a resist material over a more highly degradable material 620 covered by 610.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a temperature range, a size or distance range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

I claim:

1. A swallowable self-expanding gastric space occupying device comprising:
    a membrane through which gastric fluid can pass, wherein said membrane provides an enclosure volume separated from the gastric environment by said membrane, and said membrane is a multilayer structure comprising a sheet of first material that is partly covered with a second material, wherein said second material has a degradation rate in the gastric environment that is lower than the degradation rate of said first material in the gastric environment;
    a plurality of holes through said membrane for gastric fluid flow from the gastric environment to said enclosure volume, wherein said holes have a perimeter surface region comprising said first material having an inner surface and an outer surface, wherein said inner surface and said outer surface are not covered by said second material; and
    a plurality of self-expanding components, wherein said components are contained in said enclosure volume;
    wherein said components expand in volume upon contact with said gastric fluid, thereby expanding said device from an unexpanded volume to an expanded volume.

2. The device of claim 1, wherein said membrane maintains physical integrity in said gastric environment for 72 hours or greater.

3. The device of claim 1, wherein said components are provided as a powder.

4. The device of claim 1, wherein said components are not substantially biodegradable.

5. The device of claim 1, wherein said components comprise a hydrogel material.

6. The device of claim 1, wherein said component is made from a material selected from the group consisting of:
    a. polyacrylamide;
    b. polyethelene oxide;
    c. poly AMPS;
    d. polyvinylalcohol;
    e. sodium polyacrylate; and
    f. acrylates.

7. The device of claim 1, wherein said membrane has at least a portion that is selected from the group consisting of:
    a. a mesh;
    b. a porous layer;
    c. a tortuous passage;
    d. a woven fabric;
    e. a welded material;
    f. a sutured material; and
    g. a tied material.

8. The device of claim 1, wherein said membrane is formed into a geometric shape that comprises invaginations to accommodate expansion of said components.

9. The device of claim 8, wherein said device further comprises an encapsulation layer that surrounds said membrane.

10. The device of claim 1, wherein said membrane is elastic.

11. The device of claim 1, wherein each of said expanded components has an individual volume that is sufficiently small to exit the stomach through the pyloric sphincter and that will not cause a small bowel obstruction.

12. The device of claim 1, wherein said device has an expanded volume that is greater than or equal to 20 cm$^3$ and a shape that prevents said device from passing out of the stomach through the pyloric sphincter.

13. The device of claim 1, wherein the ratio of said expanded to unexpanded volume is selected from a range that is greater than 100 times and less than 250 times.

14. The device of claim 1, wherein said membrane maintains physical integrity in the stomach for a time range that is greater than or equal to one week and less than or equal to two months.

15. The device of claim 1, wherein said membrane comprises three layers, with said sheet of first material forming a middle layer having an inner-facing surface and an outer-facing surface, and said second material partly covers said inner-facing surface to form an inner layer and partly covers said outer-facing surface to form an outer layer.

16. A method of making a weight loss device, said method comprising:
  a. providing a plurality of self-expanding components, wherein said components expand upon contact with a gastric fluid and said components do not substantially degrade when in contact with said gastric fluid; and
  b. enveloping said plurality of self-expanding components with a membrane having a plurality of holes for gastric fluid flow through said membrane to contact said components and said membrane is capable of accommodating expansion of said components without rupture, and said membrane is a multilayer structure comprising a sheet of first material that is partly covered with a second material, wherein said second material has a degradation rate in the gastric environment that is lower than the degradation rate of said first material in the gastric environment, and wherein said holes have a perimeter surface region comprising said first material having an inner surface and an outer surface, wherein said inner surface and said outer surface are not covered by said second material.

17. The method of claim 16, wherein said membrane is substantially inelastic and said enveloping step further comprises:
  a. providing invaginations in said enveloped membrane to accommodate volume expansion of said components upon contact with gastric fluid.

18. The method of claim 16, wherein said membrane comprises a material that degrades or dissolves over time in the stomach, thereby releasing said components.

19. The method of claim 16, wherein upon substantial degradation of said first material said plurality of self-expanding compounds are released from within said envelope to the gastric environment during use.

20. The method of claim 19, wherein said membrane is formed by:
  a. providing a plurality of structural elements made of said second material, wherein each of said structural elements has a size that is sufficiently small to pass from a gastric environment through a pyloric valve;
  b. connecting each of said structural elements to adjacent structural elements by said first material; and
  c. selectively degrading said first material, thereby releasing said plurality of structural elements and self-expanding components to the gastric environment, wherein said elements and components are capable of passing through the GI tract without substantial degradation.

21. The method of claim 16, wherein said membrane comprises three layers, with said sheet of first material forming a middle layer having an inner-facing surface and an outer-facing surface, and said second material partly covers said inner-facing surface to form an inner layer and partly covers said outer-facing surface to form an outer layer.

22. A method of promoting weight loss in a patient, said method comprising:
  a. positioning a plurality of self-expanding components in an internal volume formed by a membrane having a plurality of holes to form a self-expanding space occupying device, wherein said membrane is a multilayer structure comprising a sheet of first material that is partly covered with a second material, wherein said second material has a degradation rate in the gastric environment that is lower than the degradation rate of said first material in the gastric environment, and wherein said holes have a perimeter surface region comprising said first material having an inner surface and an outer surface, wherein said inner surface and said outer surface are not covered by said second material;
  b. orally ingesting said device so that said device is located in the patient's gastric space;
  c. contacting said components with gastric fluid that pass from the gastric environment through said membrane plurality of holes to said internal volume; and
  d. expanding said components upon contact with gastric fluid, thereby expanding the volume of said device in the gastric space to promote a feeling of fullness in said patient.

23. The method of claim 22 further comprising:
  a. degrading said membrane in said gastric space;
  b. releasing said plurality of self-expanded components into said gastric space, wherein each self-expanded component has an expanded volume and shape configured to prevent a small-bowel obstruction; and
  c. passing said plurality of self-expanded components out of the patient's body by passage through the gastrointestinal system, wherein said components do not substantially degrade.

24. A swallowable self-expanding gastric space occupying device comprising:
  a composite membrane through which gastric fluid can pass, wherein said membrane provides an enclosure volume separated from the gastric environment by said membrane, said membrane comprising a first and a second material having different degradation characteristics, and said membrane is a multilayer structure comprising a sheet of said first material that is partly covered with said second material, wherein said second material has a degradation rate in the gastric environment that is lower than the degradation rate of said first material in the gastric environment;
  a plurality of holes through said composite membrane, for gastric fluid flow from the gastric environment to said enclosure volume, wherein said holes have a perimeter surface region comprising said first material having an inner surface and an outer surface, wherein said inner surface and said outer surface are not covered by said second material; and a plurality of self-expanding components, wherein said components are contained in said enclosure volume and said components expand in volume upon contact with said gastric fluid, thereby expanding said device from an unexpanded volume to an expanded volume wherein said first and second materials are operably connected to each other to provide said enclosure volume and controllable degradation of said membrane in said gastric environment.

25. The device of claim 24, wherein the composite membrane has at least a portion of said first material formed into a structure that is selected from the group consisting of:

a. a suture;

b. a stitch;

c. a bond;

d. a tie; and e. a protective layer that at least partially covers a mesh opening in said membrane wherein said structure operably connects adjacent membrane pieces formed from said second material.

* * * * *